(12) United States Patent
Silvander

(10) Patent No.: US 8,101,664 B2
(45) Date of Patent: Jan. 24, 2012

(54) UREA FOAM

(75) Inventor: Mats Silvander, Uppsala (SE)

(73) Assignee: Quinnova Pharmaceuticals, Inc., Newtown, PA (US)

( * ) Notice: Subject to any disclaimer, the term of this patent is extended or adjusted under 35 U.S.C. 154(b) by 1042 days.

(21) Appl. No.: 12/016,371

(22) Filed: Jan. 18, 2008

(65) Prior Publication Data

US 2008/0175793 A1 Jul. 24, 2008

Related U.S. Application Data

(60) Provisional application No. 60/885,677, filed on Jan. 19, 2007.

(51) Int. Cl.
*A61K 9/12* (2006.01)
*A61K 31/16* (2006.01)
*A61K 31/17* (2006.01)

(52) U.S. Cl. ........ 514/588; 514/579; 514/861; 514/863; 514/945; 424/45

(58) Field of Classification Search .................. 514/579, 514/588, 861, 863, 945; 424/45
See application file for complete search history.

(56) References Cited

U.S. PATENT DOCUMENTS

| 3,666,863 | A | 5/1972 | Swanbeck | |
|---|---|---|---|---|
| 3,962,150 | A | 6/1976 | Viola | |
| 4,672,078 | A | 6/1987 | Sakai | |
| 4,801,621 | A | 1/1989 | Reischl | |
| 5,525,635 | A | 6/1996 | Moberg | |
| 5,679,324 | A | 10/1997 | Lisboa | |
| 5,919,470 | A * | 7/1999 | Valdez et al. | 424/401 |
| 5,993,830 | A | 11/1999 | Freij | |
| 2002/0168389 | A1 | 11/2002 | Chandar | |
| 2005/0042182 | A1* | 2/2005 | Arkin et al. | 424/47 |
| 2005/0049232 | A1 | 3/2005 | Lindau | |
| 2005/0250076 | A1* | 11/2005 | Rhoades | 433/217.1 |
| 2009/0068117 | A1 | 3/2009 | Day | |

FOREIGN PATENT DOCUMENTS

EP 0440298 A1 7/1991

OTHER PUBLICATIONS

Merck Manual Home Edition article entitled, "Corns and Calluses" accessed on Feb. 19, 2011 at www.merckmanuals.com/home/print/sec05/ch072/ch072j.html.*
Merck Manual Home Edition article entitled, "Dermatitis" accessed on Feb. 19, 2011 at www.merckmanuals.com/home/print/sec18/ch203/ch203c.html.*
Search Report/Written Opinion, Apr. 14, 2008, in sister PCT/US08/51444 (which mistakes a reference to a complex N-oxide as a reference to urea (a minor structural element of the N-oxide)).

* cited by examiner

*Primary Examiner* — James H. Alstrum-Acevedo
(74) *Attorney, Agent, or Firm* — Diehl Servilla LLC; Ken M. Zeidner

(57) ABSTRACT

Provided, among other things, is a delivery module for a non-greasy, water-based urea composition comprising: an aerosol delivery device; within the aerosol delivery device, the urea composition comprising 20% or more urea by weight, non-greasy lipophilic component(s), and a frothing agent, the urea composition having a viscosity low enough to support aerosol delivery, and the urea composition effective to form a foam upon propellant-driven aerosol delivery; and within the aerosol delivery device, a propellant.

20 Claims, No Drawings

UREA FOAM

The present invention relates to foam-forming composition of urea, which can be used to treat psoriasis, and thickened areas of the soles, elbows, knees and the like.

Urea, especially in high concentrations, can be used to treat dry scaly skin, or skin that has thickened to a non-cosmetic or uncomfortable degree. This activity has been attributed to the ability of urea to solubilize and denture protein. Urea can be used to treat xerosis, ichthyosis (e.g., ichthyosis vulgaris), psoriasis, atopic dermatitis, and the like. Such treatment can include itch relief, at least temporary itch relief.

Dermatological compositions of concentrated urea have been formulated in oily bases. Such a oil-based formulations provide a protective layer and localize the urea on the skin. Despite the bias in the industry to formulate in oil-based ointments, Applicant sought to make a water-based, foam-forming composition.

In seeking to formulate a water-based, foam-forming composition, it was discovered that high urea concentrations destabilize formulations that are otherwise stable, water-based dermatological formulations, yielding compositions that form sediments to a degree that makes proper dispensing difficult. Described herein are parameters within which one can formulate stable, water-based compositions of urea at high concentration.

SUMMARY OF THE INVENTION

Provided, among other things, is a delivery module for a non-greasy, water-based urea composition comprising: an aerosol delivery device; within the aerosol delivery device, the urea composition comprising 20% or more urea by weight, non-greasy lipophilic component(s), and a frothing agent, the urea composition having a viscosity low enough to support aerosol delivery, and the urea composition effective to form a foam upon propellant-driven aerosol delivery; and within the aerosol delivery device, a propellant.

Further provided, among other things, is a urea composition comprising: urea 20-50%; fatty acid(s) and/or analogous alkyl amine(s) 1-5%; hydrophilic polymer(s) 0.5-1.5%; titrant, as needed in amount effective to substantially neutralize the fatty acid(s) or alkyl amine(s); frothing agent 0.3-4%; and humectant 0.5-7%.

Also provided, among other things, is a method of treating dermatitis, psoriasis, xerosis, ichthyosis, eczema, keratosis, keratoderma, dry and rough skin, corns, calluses, damaged, or ingrown and devitalized nails comprising applying to affected skin a foamed, non-greasy, water-based urea composition comprising: 20% or more urea by weight, non-greasy lipophilic component(s), and a frothing agent, the urea composition having a viscosity low enough to support aerosol delivery, and the urea composition effective to form a foam upon propellant-driven aerosol delivery.

DETAILED DESCRIPTION OF THE INVENTION

Urea can be present, for example, in amounts from about 20% by weight to to about 50% by weight, or to about saturation (in the composition). Unless otherwise detailed, all amount percentages presented in this specification are weight percentages. In certain embodiments, urea is 20% or more, 25% or more, 30% or more, 31% or more, or 32% or more, or 33% or more, or 34% or more, or 35% or more, or 36% or more, or 37% or more, or 38% or more, or 39% or more of the urea composition. In certain embodiments, urea is 49% or less, or 48% or less, or 47% or less, or 46% or less, or 45% or less, or 44% or less, or 43% or less, or 42% or less, or 41% or less of the urea composition.

It is believed that urea formulated in an aqueous solution can facilitate urea absorption on skin. A non-greasy skin-feel, which can be achieved with the present formulation, allows for more frequent applications than would be cosmetically acceptable with oil based formulations.

The composition can contain lipophilic components that are believed to help distribute urea on and into the skin. A major portion of such lipophilic components can be amphiphates in amounts effective to stabilize the lipophilic components in solution and/or emulsified. Example amphiphates are fatty acids, which can be substantially or essentially ionized, wherein the salt is soluble in the aqueous solution of the urea composition. Further examples are alkyl amines with one alkyl per amine having a size distribution analogous to that of an appropriate fatty acid composition. Further examples are nonionic detergents.

The fatty acid can, for example, be of any composition found in a natural source, including hydrolysis of esterified fatty acids. Or, the fatty acid component can be hydrogenated to remove substantially all or a portion of any unsaturation. In certain embodiments, the fatty acid component or the alkyl moiety of the alkyl amine component is selected such that 50 mole % or more is C12 or higher, or C14, or C16 or higher. In certain embodiments, the fatty acid component or the alkyl moiety of the alkyl amine component is selected such that 50 mole % or more is C22 or lower, or C20 or lower, or C18 or lower. In certain embodiments, 75 mole % or more of the fatty acid component is from C12 or C14 or C16 to C22 or C20 or C18. In certain embodiments, 80 mole % or more, 85 mole % or more, 90 mole % or more, 95 mole % or more, 97 mole % or more, 98 mole % or more, or 99 mole % or more, meets one of the size parameters of this paragraph.

For carboxylic acid containing lipophilic components, useful salts include the alkali metal salts such as sodium or potassium salts; ammonium salts; salts formed with suitable organic bases, such as amine salts (such as triethyl amine, triethanol amine, or the like) and quaternary ammonium salts; or the like. Bivalent or trivalent salts can be used where they do not adversely affect solubility. For amine-containing lipophilic components, useful salts include maleates, fumarates, lactates, oxalates, methanesulfonates, ethanesulfonates, benzenesulfonates, tartrates, citrates, halides (e.g., hydrochlorides, hydrobromides), sulfates, phosphates, nitrates, and the like. As needed, the lipophilic components are provided such that a sufficient amount of constituent ionizable molecules are in ionized (salt) form to provide solubility. Such ionized forms can be prepared by adding a titrant, though recitations of compositions described by such titration include the equivalent compositions formed by pre-formed salts or otherwise.

The lipophilic component may include 50% or less of a more hydrophobic component, such as one that can be termed an emollient. This more hydrophobic component can be, for example, 45% or less, or 40% or less, or 35% or less, or 30% or less, or 25% or less, or 20% or less, of the lipophilic component.

In certain embodiments, the lipophilic component is 1% or more, or 1.5% or more, or 2% or more, or 2.5% or more, or 3% or more of the urea composition. In certain embodiments, the lipophilic component is 8% or less, 7.5% or less, 7% or less, 7.5% or less, 6% or less, 5.5% or less, 5% or less, or 4.5% or less, or 4% or less, or 3.5% or less of the urea composition. Where the lipophilic component comprises, as predominant component(s), fatty acids or analogous alkyl amines, these predominate components can be 1% or more, or 1.5% or more, or 2% or more, or 2.5% or more, or 3% or more of the urea composition; and 5% or less, or 4.5% or less, or 4% or less, or 3.5% or less of the urea composition.

An emollient, if present, can be a silicone oil such as polydimethylsiloxane (i.e., dimethicone), petrolatum, or the like. In certain embodiments, the emollient(s) are 0.5% or more, or 0.6% or more, or 0.7% or more, or 0.8% or more, or 0.9% or more, or 1% or more of the urea composition. In certain embodiments, the emollient(s) are 2% or less, or 1.9% or less, or 1.8% or less, or 1.7% or less, or 1.6% or less, or 1.5% or less, or 1.4% or less, or 1.3% or less, or 1.2% or less, or 1.1% or less, or 1% or less of the urea composition.

A non-greasy feel is measured in reference to oil-based ointments and by comparison of the feel of the Example composition (described in the Example below), applied to skin at 1 mg/cm$^2$, compared to the oil-based product described in the Table at Column 3 of U.S. Pat. No. 5,919,470 (Bradley Pharmaceuticals, Inc.), applied in the same amount. While the feel of compositions of the invention may vary, in making the comparison between the non-greasy standard, the greasy standard, and the prospective non-greasy composition, it will be apparent which category the prospective composition falls within. The non-greasy skin feel may be moist and smooth feeling, but the difference in greasy feel relative to the greasy comparative shall be clear.

The hydrophilic polymer(s) can be any non-toxic water soluble polymer(s) that (in the aggregate) stabilize foam and contribute to film formation on the skin. Examples include polyvinyl pyrrolidone, polyethylene glycol, starch, water-soluble derivatives of starch, cellulose, methyl cellulose, hydroxymethylcellulose, other water-soluble derivatives of cellulose, carbomers, or the like. For polyvinyl pyrrolidone, for example, useful average molecular weights include from 8,000 to 63,000, such as about 38,000. For all polymers used in the composition, the size should be sufficient to limit penetration of the horny layer of the skin, if skin penetration is an issue for the given polymer.

In certain embodiments, hydrophilic polymer(s) are 0.2% or more, 0.3% or more, 0.4% or more, 0.5% or more, or 0.6% or more, or 0.7% or more, or 0.8% or more, or 0.9% or more, or 1% or more, or 1.5% or more of the urea composition. In certain embodiments, the hydrophilic polymer(s) are 3% or less, 2.5% or less, 2% or less, 1.5% or less, or 1.4% or less, or 1.3% or less, or 1.2% or less, or 1.1% or less, or 1% or less of the urea composition.

The composition can also contain a humectant, such as glycerol, propylene glycol, other polyols, polydextrose, lactic acid, or the like. In certain embodiments, humectant(s) are 0.5% or more, or 0.6% or more, or 0.7% or more, or 0.8% or more, or 0.9% or more, or 1% or more, or 1.2% or more, or 1.4% or more, or 1.6% or more, or 1.8% or more, or 2% or more, or 2.5% or more, or 3% or more, or 3.5% or more, or 4% or more of the urea composition. In certain embodiments, the humectant(s) are 7% or less, or 6.5% or less, or 6.0% or less, or 5.8% or less, or 5.6% or less, or 5.4% or less, or 5.2% or less, or 5% or less of the urea composition.

The frothing agent can be, for example, a non-ionic detergent such as Polysorbate 20, polyoxyethylene sorbitan fatty acid esters, sorbitol fatty acid esters, or the like. In certain embodiments, the frothing agent(s) are 0.3% or more, or 0.4% or more, or 0.5% or more, or 0.6% or more, or 0.7% or more, or 0.8% or more, or 0.9% or more, or 1% or more, or 1.1% or more, or 1.2% or more, or 1.3% or more, or 1.4% or more, or 1.5% or more, or 1.6% or more, or 1.7% or more, or 1.8% or more, or 1.9% or more, or 2.0% or more, or 2.1% or more, or 2.2% or more, or 2.3% or more of the urea composition. In certain embodiments, the frothing agent(s) are 4% or less, 3.5% or less, 3% or less, 2.9% or less, 2.8% or less, 2.7% or less, 2.6% or less, 2.5% or less, 2.4% or less, 2.3% or less, 2.2% or less, 2.1% or less, 2% or less, 1.9% or less, 1.8% or less, 1.7% or less, 1.6% or less, 1.5% or less, or 1.4% or less, or 1.3% or less, or 1.2% or less, or 1.1% or less, or 1% or less, or 0.9% or less, or 1.8% or less of the urea composition.

In certain embodiments, the urea composition can contain soothing agent(s) such as homogenized oatmeal. In certain embodiments, the soothing agent(s) are 0.02% or more, 0.03% or more, 0.04% or more, 0.05% or more, or 0.06% or more, or 0.07% or more, or 0.08% or more, or 0.09% or more, or 0.01% or more of the urea composition. In certain embodiments, the soothing agent(s) are 0.2% or less, or 0.15% or less, or 0.14% or less, or 0.13% or less, or 0.12% or less, or 0.11% or less, or 1% or less of the urea composition.

Additional optional ingredients include sunscreens, antimicrobial agents or preservatives, fragrances, and the like.

Suitable propellants include, for example, propane, butane, isobutene, other hydrocarbons, hydrofluorocarbons, chlorofluorocarbons (Cl/F/(H)/C), and the like.

The amount of urea composition applied to an affected area of skin can vary with a number of variables including the condition of the skin, the sensitivity of the patient or the area of skin, and the like. In any single administration, the delivery device can deliver to the affected area an appropriate layer of foam that provides an appropriate amount of urea composition. The aerosol-driven foam can be applied to the affected area and rubbed into the skin until absorbed. Typically, the composition is applied twice a day.

Topically applied urea is believed to dissolve the intercellular matrix of the skin which results in enhanced shedding of scaly, dry skin and thus a softening of the hyperkeratotic areas of the skin. Urea topically applied to the nail plate has a similar effect on the intercellular matrix of the nail plate. Topically applied urea can be used for enzymatic debridement and promotion of normal healing of surface lesions, particularly where healing is retarded by local infection, necrotic tissue, fibrinous or purulent debris, or eschar. Topically applied urea is useful for the treatment of hyperkeratotic conditions such as dermatitis (e.g., atopic dermatitis), psoriasis, xerosis, ichthyosis, eczema, keratosis, keratoderma, dry, rough skin, corns and calluses, damaged, ingrown and devitalized nails, and the like.

EXAMPLE 1

The following composition is formulated:

| Component | Wt. % |
| --- | --- |
| Water | 46.47 |
| PVP | 0.95 |
| Oatmeal | 0.1 |
| Stearic acid | 3.13 |
| Propylene Glycol | 2.9 |
| Glycerin | 2.0 |
| Dimethicone | 1.0 |
| Phenonipe ™ (a mixture of preservatives from _____) | 0.5 |
| Triethanol amine | 0.65 |
| Polysorbate 20 | 2.30 |
| Urea | 40.0 |
| Total | 100.00 |

The oatmeal is homogenized in a portion of the water. The remaining water is heated to 70° C. With stirring, the following were added in order: PVP, oatmeal slurry, and stearic acid. Then, the remainder is added less the urea. The temperature controller is set to 60° C., allowing the temperature to decline. When the temperature is down to 60° C., the urea is added in portions as follows: 8 parts of 100, 8 parts, 8 parts, 16 parts, 16 parts, 16 parts, remainder. Care is taken that the temperature is 60° C. or higher on each addition. The regulator is then set to 25° C., and the composition is agitated for 30 minutes. Aerosol dispensers can be filled with the composition at 25° C.

Or, The water is heated to 70° C. With stirring, the following were added in order: oatmeal, PVP, and stearic acid. Then, the remainder is added less the urea. The temperature controller is set to 60° C., allowing the temperature to decline. When the temperature is down to 60° C., the urea is added in portions as follows: 8 parts of 100, 8 parts, 8 parts, 16 parts, 16 parts, 16 parts, remainder. Care is taken that the temperature is 60° C. or higher on each addition. After the last urea addition, and after the temperature has again reached 60° C., the regulator is then set to 25° C., and the composition is agitated for 30 minutes. Aerosol dispensers can be filled with the composition at 25° C., and with stirring during filling.

EXAMPLE 2

The following composition is formulated:

| Component | Wt. % |
|---|---|
| Water | 48.07 |
| PVP | 0.95 |
| Oatmeal | 0.1 |
| Stearic acid | 3.13 |
| Propylene Glycol | 2.9 |
| Glycerin | 2.0 |
| Dimethicone | 1.0 |
| Phenonipe ™ (a mixture of preservatives from _____) | 0.5 |
| Triethanol amine | 0.65 |
| Polysorbate 20 | 0.70 |
| Urea | 40.0 |
| Total | 100.00 |

The oatmeal is homogenized in a portion of the water. The remaining water is heated to 70° C. With stirring, the following were added in order: PVP, oatmeal slurry, and stearic acid. Then, the remainder is added less the urea. The temperature controller is set to 40° C., allowing the temperature to decline. When the temperature is down to 50° C., the urea is added in portions as follows: 8 parts of 100, 8 parts, 8 parts, 16 parts, 16 parts, 16 parts, remainder. Care is taken that the temperature is 40° C. or higher on each addition. The regulator is then set to 25° C., and the composition is agitated for 30 minutes. Aerosol dispensers can be filled with the composition at 25° C.

Or, The water is heated to 70° C. With stirring, the following were added in order: oatmeal, PVP, and stearic acid. Then, the remainder is added less the urea. The temperature controller is set to 40° C., allowing the temperature to decline. When the temperature is down to 50° C., the urea is added in portions as follows: 8 parts of 100, 8 parts, 8 parts, 16 parts, 16 parts, 16 parts, remainder. Care is taken that the temperature is 40° C. or higher on each addition. After the last urea addition, and after the temperature has again reached 40° C., the regulator is then set to 25° C., and the composition is agitated for 30 minutes. Aerosol dispensers can be filled with the composition at 25° C., and with stirring during filling.

DEFINITIONS

The following terms shall have, for the purposes of this application, the respective meanings set forth below.

Effective Amount

To treat the indications of the invention, an effective amount of a urea will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. In effective amount can be a dermatological treatment effective concentration of urea.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A non-greasy, water-based urea composition comprising, by weight:
   urea 20-50%;
   one or more fatty acids or alkyl amines 1-5%;
   one or more hydrophilic polymers 0.5-1.5%;
   a titrant;
   a frothing agent 0.3-4%;
   a humectant 0.5-7%, and
   homogenized oatmeal 0.02-0.2%.

2. The urea composition of claim 1, wherein the urea composition comprises 0.3-1.5% frothing agent by weight.

3. The urea composition of claim 1, wherein the urea composition further comprises 0.5-2% emollient by weight.

4. The urea composition of claim 1, wherein the urea composition comprises 30-50% urea.

5. The urea composition of claim 4, wherein the urea composition comprises 35-45% urea.

6. The urea composition of claim 1, wherein the titrant is triethanolamine.

7. The urea composition of claim 1, wherein the one or more hydrophilic polymers are selected from polyvinyl pyrrolidone, polyethylene glycol, starch, cellulose, methyl cellulose, hydroxymethyl cellulose, other water-soluble derivatives of cellulose, water soluble derivatives of starch, or carbomers.

8. The urea composition of claim 1, wherein the urea composition further comprises a propellant.

9. The urea composition of claim 8, wherein the propellant is selected from propane, butane, isobutene, other hydrocarbons, hydrofluorocarbons, or chlorofluorocarbons.

10. The urea composition of claim 1, wherein the humectant is selected from glycerol, propylene glycol, other polyols, polydextrose, or lactic acid.

11. The urea composition of claim 10, wherein the humectant is lactic acid.

12. The urea composition of claim 1, wherein the titrant is present in an amount effective to neutralize the one or more fatty acids or alkyl amines.

13. A non-greasy, water-based urea composition comprising, by weight
   urea in the range of 35-45%
   a hydrophilic polymer that is polyvinyl pyrrolidone (PVP) in the range of 0.5-2%;
   a soothing agent that is oatmeal in the range of 0.02-0.2%;
   a fatty acid that is stearic acid in the range of 1-5%;
   a humectant that comprises propylene glycol and glycerin in the range of 2-5%;
   an emollient that is dimethicone in the range of 0.5-2%;
   one or more preservatives;
   a titrant that is triethanolamine; and
   a frothing agent that is polysorbate 20 in the range of 0.3-4%;
   and the balance being water.

14. The urea composition of claim 13, wherein the titrant is present in an amount effective to neutralize the fatty acid.

15. The urea composition of claim 13, further comprising a propellant.

16. A method of treating one or more indications of dermatitis, psoriasis, xerosis, ichthyosis, eczema, keratosis, keratoderma, dry and rough skin, corns, calluses, damaged, or ingrown and devitalized nails comprising applying to affected skin a foamed, non-greasy, water-based urea composition comprising, by weight:
   20-50% urea, a non-greasy lipophilic component comprising one or more fatty acids or alkyl amines in the range of 1-5%, one or more hydrophilic polymers in the range of 0.5-1.5%, a frothing agent in the range of 0.3-4%, a titrant, a humectant in the range of 0.5-7%, and homogenized oatmeal in the range of 0.02-0.2%,
   the urea composition having a viscosity effective to provide aerosol delivery, and the urea composition effective to form a foam upon propellant-driven aerosol delivery.

17. The method of claim 16, wherein the urea composition further comprises 0.5-2% emollient by weight.

18. The method of claim 16, wherein the urea composition comprises 30-50% urea.

19. The method of claim 18, wherein the urea composition comprises 35-45% urea.

20. The method of claim 16, wherein the titrant is present in an amount effective to neutralize the one or more fatty acids or alkyl amines.

* * * * *